(12) United States Patent
Christoffel et al.

(10) Patent No.: US 6,582,412 B2
(45) Date of Patent: Jun. 24, 2003

(54) DISPOSABLE ONE-PIECE SWIMSUIT FOR GIRLS

(75) Inventors: Sarah L. Christoffel, Appleton, WI (US); Catherine M. Hancock-Cooke, Neenah, WI (US); Marci E. Sojka, Neenah, WI (US); Laurie Couture-Dorschner, Hortonville, WI (US); Louise C. Coe, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 264 days.

(21) Appl. No.: 09/751,374

(22) Filed: Dec. 29, 2000

(65) Prior Publication Data

US 2002/0087137 A1 Jul. 4, 2002

(51) Int. Cl.⁷ .................................. A61F 13/15
(52) U.S. Cl. ............ 604/385.01; 604/375; 604/385.03; 604/385.22; 604/385.28; 604/386; 2/67
(58) Field of Search ................. 604/385.01, 375, 604/385.03, 385.22, 385.28, 386; 2/67

(56) References Cited

U.S. PATENT DOCUMENTS

| | | | |
|---|---|---|---|
| 1,865,029 A | * 6/1932 | Martz | ............... 2/67 |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,100,324 A | 7/1978 | Anderson et al. | |
| D249,096 S | 8/1978 | Fowler | |
| D259,671 S | 6/1981 | Joseph | |
| D259,672 S | 6/1981 | Joseph | |
| D259,821 S | 7/1981 | Myles | |
| D261,822 S | 11/1981 | Joseph | |
| 4,301,545 A | 11/1981 | Camarena | |
| D264,516 S | 5/1982 | Joseph | |
| 4,340,563 A | 7/1982 | Appel et al. | |
| D268,542 S | 4/1983 | Johnson | |
| D269,220 S | 6/1983 | Joseph | |
| D275,810 S | 10/1984 | Myles | |
| D278,474 S | 4/1985 | Briggery Myles | |
| D278,476 S | 4/1985 | Briggery Myles | |
| D278,568 S | 4/1985 | Briggery Myles | |
| D278,569 S | 4/1985 | Briggery Myles | |

(List continued on next page.)

FOREIGN PATENT DOCUMENTS

| | | |
|---|---|---|
| EP | 0 217 032 | 4/1987 |
| FR | 2690316 | 10/1993 |
| IL | 88675 | 5/1991 |
| JP | 08-013208 | 1/1996 |
| SE | 82/02552 | 11/1983 |
| WO | 96/03950 | 2/1996 |
| WO | 96/36248 | 11/1996 |
| WO | 97/31603 | 9/1997 |

OTHER PUBLICATIONS

US 5,915,536, 6/1999, Alberts et al. (withdrawn)

*Primary Examiner*—John J. Calvert
*Assistant Examiner*—Angela J. Grayson
(74) *Attorney, Agent, or Firm*—Pauley Petersen Kinne & Erickson

(57) ABSTRACT

A disposable, one-piece swimsuit for girls includes a bodice attached to a chassis. The bodice is designed to provide upper torso coverage while the chassis can include absorbent and containment features. The upper torso coverage contributes to social decency and also protects the wearer's skin against excessive exposure to the sun. The absorbent and containment features can either be integrated within the chassis or can be in the form of a separate, pant-like, absorbent garment covered by the chassis.

35 Claims, 10 Drawing Sheets

U.S. PATENT DOCUMENTS

| | | |
|---|---|---|
| D279,420 S | 7/1985 | Johnson |
| D279,936 S | 8/1985 | Myles |
| D280,252 S | 8/1985 | Briggery Myles |
| D282,116 S | 1/1986 | Myles |
| 4,656,669 A | 4/1987 | Beard |
| 4,663,220 A | 5/1987 | Wisneski et al. |
| D290,300 S | 6/1987 | Petruzzi |
| 4,704,116 A | 11/1987 | Enloe |
| 4,815,145 A | 3/1989 | Chow |
| 4,818,464 A | 4/1989 | Lau |
| 4,928,323 A | 5/1990 | Nathan |
| D308,900 S | 7/1990 | Gabriels |
| 4,940,464 A | 7/1990 | Van Gompei et al. |
| 4,972,522 A | 11/1990 | Rautenberg |
| 5,046,272 A | 9/1991 | Vogt et al. |
| 5,224,405 A | 7/1993 | Pohjola |
| 5,226,992 A | 7/1993 | Morman |
| D339,900 S | 10/1993 | Fanning |
| 5,380,578 A | 1/1995 | Rautenberg |
| 5,388,275 A | 2/1995 | Oram |
| 5,423,789 A | 6/1995 | Kuen |
| 5,452,477 A | 9/1995 | Mann |
| 5,592,690 A | 1/1997 | Wu |
| 5,634,216 A | 6/1997 | Wu |
| 5,683,373 A | 11/1997 | Darby |
| 5,711,034 A * | 1/1998 | Cillik .................... 2/406 |
| 5,717,998 A * | 2/1998 | Everett et al. ............ 2/67 |
| 5,776,123 A | 7/1998 | Goerg et al. |
| 5,790,983 A | 8/1998 | Rosch et al. |
| 5,810,800 A * | 9/1998 | Hunter et al. .......... 604/385.23 |
| D406,188 S | 3/1999 | Costello |
| 5,876,394 A | 3/1999 | Rosch et al. |
| D409,818 S | 5/1999 | Shaffer |
| 5,904,675 A | 5/1999 | Laux et al. |
| 5,907,872 A | 6/1999 | Alberts et al. |
| 5,931,825 A | 8/1999 | Kuen et al. |
| D413,424 S | 9/1999 | Davies et al. |
| 5,953,754 A | 9/1999 | Rosch et al. |
| D416,124 S | 11/1999 | Davies et al. |
| 6,006,364 A | 12/1999 | Newsom et al. |
| 6,009,558 A | 1/2000 | Rosch et al. |
| 6,035,439 A | 3/2000 | Chin |
| 6,163,884 A | 12/2000 | Rosch et al. |

* cited by examiner

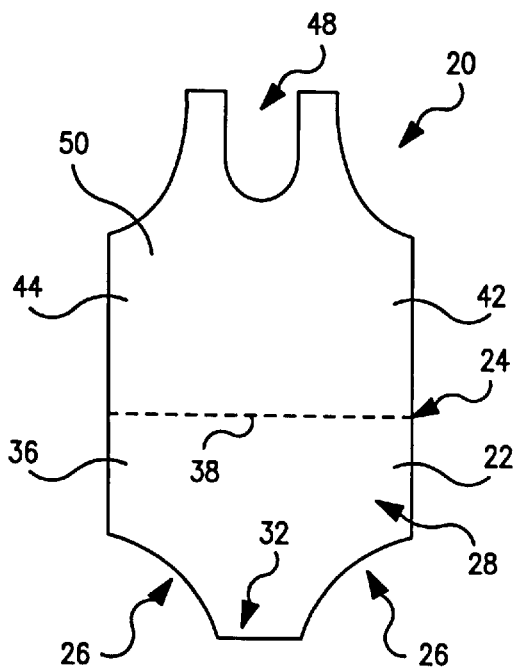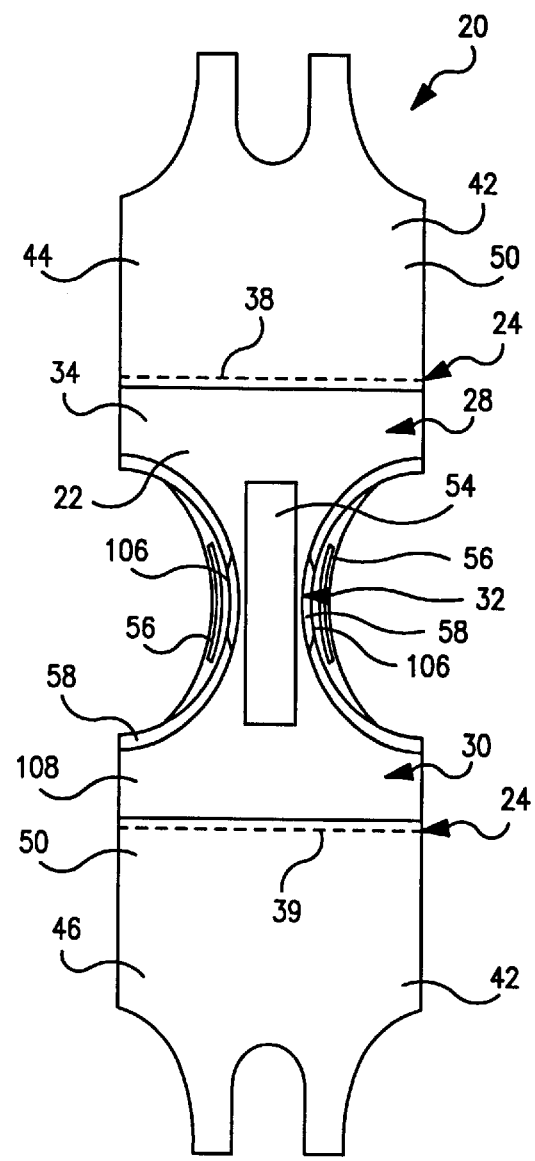

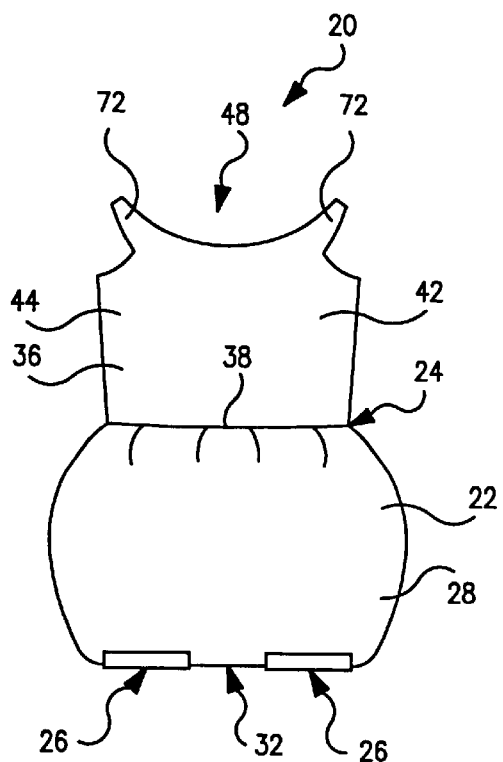
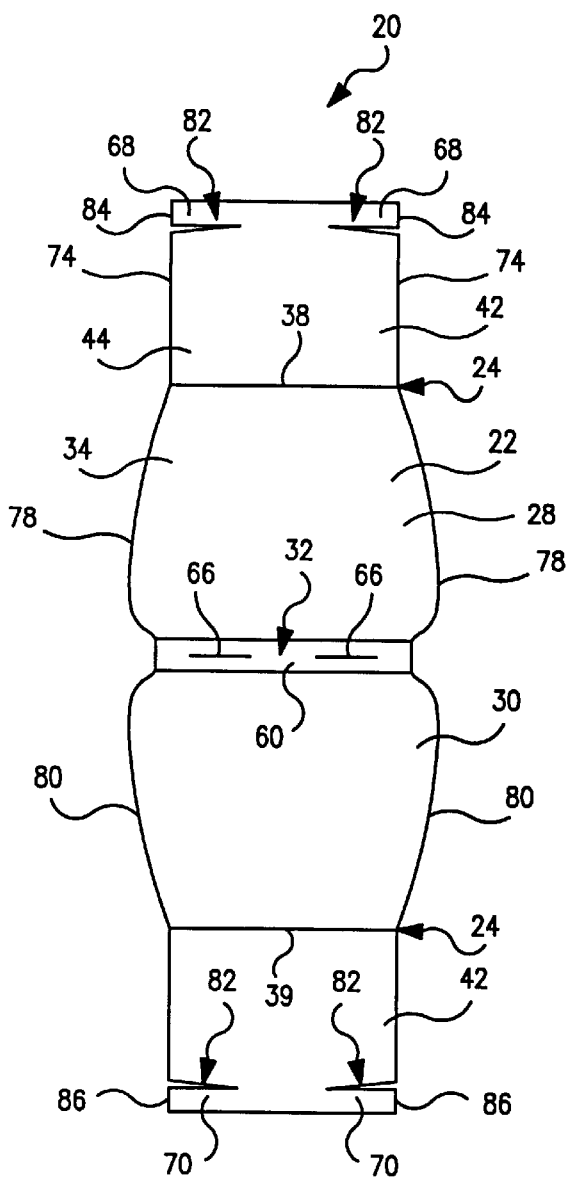
FIG. 6
FIG. 7

DISPOSABLE ONE-PIECE SWIMSUIT FOR GIRLS

FIELD OF THE INVENTION

This invention is directed to a disposable one-piece swimsuit for girls, having absorbent and containment features.

BACKGROUND OF THE INVENTION

Absorbent swim pants and swimsuits for pre-toilet trained kids are typically pant-like garments, resembling diapers or training pants, that lack any coverage for the wearer's upper torso. These garments are appropriate for boys, but can be considered inadequate for girls. In our society, girls do not typically expose their bare frontal upper torsos. Babies can be considered an exception to this general rule, but for the most part, even female infants and toddlers are typically dressed in a way to cover their upper torsos.

Some clothing manufacturers make cloth swimsuits that provide upper torso coverage for female infants and toddlers, but these swimsuits generally provide no containment qualities and, furthermore, must be washed after each use, which can be a very undesirable task, particularly when the wearer urinates, or worse, creates solid waste in the garment. Absorbent swimpants can be worn underneath a cloth swimsuit.

There is a need or desire for a disposable swimwear garment that provides upper torso coverage for female wearers.

SUMMARY OF THE INVENTION

The present invention is directed to a one-piece disposable swimsuit, particularly suitable for female infants and toddlers, that provides upper torso coverage as well as absorbent and containment features. In addition to satisfying the social norm of covering up girls' frontal upper torsos, the upper torso coverage provided in this invention also provides protection from the sun against harmful rays that could lead to sunburn, or worse, skin cancer.

The swimsuit of the invention is disposable, such that it can be worn for a limited time, until the garment is soiled or for the duration of the wearer's water activities. The swimsuit can be a conventionally shaped tanksuit, with primarily cross-body stretch, suitably with areas of differential stretch to improve fit. Alternatively, various non-conventional designs are also included herein. These various designs all provide frontal upper torso coverage in combination with absorbent and containment features. An absorbent assembly located within the crotch area of the swimsuit is suitably pulp-based and will not swell when wet. Additionally, containment flaps can be attached around the leg openings to provide enhanced containment of bowel movements.

With the foregoing in mind, it is a feature and advantage of the invention to provide a disposable, one-piece swimsuit that provides frontal upper torso coverage as well as absorbent and containment features.

BRIEF DESCRIPTION OF THE DRAWINGS

FIG. 1 is a front perspective view of a one-piece disposable swimsuit;

FIG. 2 is a plan view of the one-piece disposable swimsuit in FIG. 1 in a partially disassembled, stretched flat state;

FIG. 6 is a front perspective view of a one-piece disposable swimsuit;

FIG. 7 is a plan view of the one-piece disposable swimsuit in FIG. 6 in a partially disassembled, stretched flat state;

DEFINITIONS

Figure 3:
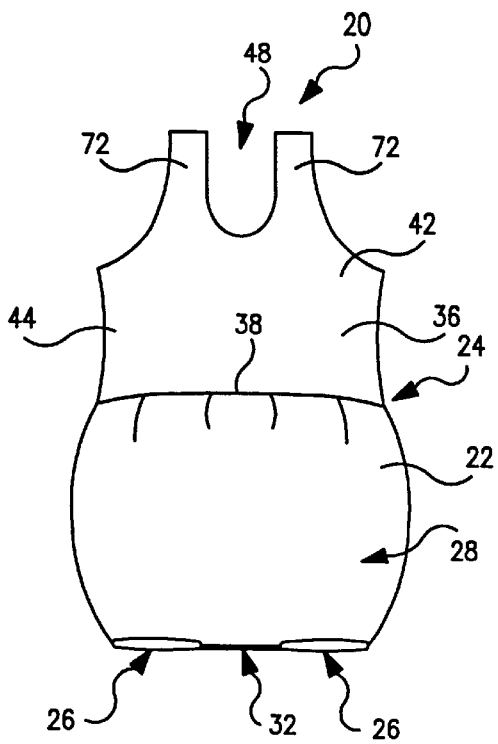
FIG. 3 is a front perspective view of a one-piece disposable swimsuit.

Within the context of this specification, each term or phrase below will include the following meaning or meanings.

"Airlaid" refers to a process for making material wherein fibers, such as cellulose-type fibers, are arranged on a wire where they are sprayed with an adhesive. The airlaid material is thus an adhesive-bonded material.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Coform" refers to a process in which at least one meltblown diehead is arranged near a chute through which other materials are added to the web while it is forming. Such other materials may be pulp, superabsorbent particles, cellulose or staple fibers, for example. Coform processes are shown in commonly assigned U.S. Pat. No. 4,818,464 to Lau and U.S. Pat. No. 4,100,324 to Anderson et al. Webs produced by the coform process are generally referred to as coform materials.

"Cross-body direction" refers to the direction generally perpendicular to a person's spinal cord.

"Disposable" refers to articles which are designed to be discarded after a limited use rather than being laundered or otherwise restored for reuse. Such articles are not generally laundered or otherwise restored for resumed use after undergoing the intended use.

"Elastic," "elasticized" and "elasticity" mean that property of a material or composite by virtue of which it tends to recover its original size and shape after removal of a force causing a deformation.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Layer" when used in the singular can have the dual meaning of a single element or a plurality of elements.

"Liquid-impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid-impermeable" when used herein.

"Liquid-permeable material" or "liquid water-permeable material" refers to a material present in one or more layers, or in components, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material, but may be small enough to limit flow of liquid water only above a minimum hydrostatic pressure.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self-bonding when deposited onto a collecting surface. Meltblown fibers used in the present invention are preferably substantially continuous in length.

"Non-stretchable" means that a material can only be stretched, without breaking, to less than 150% of its initial (unstretched) length in at least one direction, suitably less than 130% of its initial length, desirably less than 110% of its initial length.

"Nonwoven" and "nonwoven web" refer to materials and webs of material which are formed without the aid of a textile weaving or knitting process.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Staple fibers" refers to non-continuous fibers. Staple fibers are produced with a conventional fiber spinning process and then cut to a staple length, from about 1 inch to about 8 inches. Such staple fibers are subsequently carded, wet-laid, or air-laid and then thermally bonded to form a nonwoven web.

"Stretchable" means that a material can be stretched, without breaking, by at least 50% (to at least 150% of its initial (unstretched) length) in at least one direction, suitably by at least 100% (to at least 200% of its initial length), desirably by at least 150% (to at least 250% of its initial length). The term includes elastic materials as well as materials that stretch but do not significantly retract.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a one-piece disposable swimwear garment, particularly suitable for female infants and toddlers. The swimwear garment can include absorbent and containment features within the garment, or can provide room for a separate, pant-like, absorbent garment underneath the swimwear garment.

Referring to FIGS. 1–13, several embodiments of the swimsuit 20 of the invention are illustrated. The swimsuit 20 includes a chassis 22. The chassis 22 defines a waist region 24, a pair of leg openings 26, a front region 28, a back region 30, a crotch region 32 interconnecting the front and back regions 28, 30 between the leg openings 26, an inner surface 34 which is configured to contact the wearer, and an outer surface 36 opposite the inner surface 34 which is configured to contact the wearer's clothing if the wearer is wearing any outer clothing. Front and back waist edges 38 and 39 of the chassis 22 are configured to encircle the waist of the wearer when worn and define a waist perimeter dimension.

The swimsuit 20 also includes a bodice 42. The bodice 42 defines a front region 44, a back region 46 and a neck opening 48 between the front region 44 and the back region 46. Like the chassis 22, the bodice 42 also includes an inner surface 34 which is configured to contact the wearer, and an outer surface 36 opposite the inner surface 34 which is configured to contact the wearer's clothing if the wearer is wearing any outer clothing.

The bodice 42 is attached to the chassis 22 about the waist region 24. The waist region 24 is the region roughly between the bottom of a wearer's rib cage and the wearer's pelvis. The chassis 22 and the bodice 42 can be attached to one another about the full circumference of the wearer's waist, in which case the chassis 22 and the bodice 42 can either be two separate entities bonded together or one continuous coverstock 50, or outer cover. Alternatively, the bodice 42 can extend only partially around the circumference of the wearer's waist, in which case, once again, the chassis 22 and the bodice 42 can either be two separate entities bonded together or one continuous coverstock 50.

An embodiment of a swimsuit 20 having the chassis 22 and the bodice 42 as one continuous coverstock 50 is shown in FIG. 1. The swimsuit 20 looks like a typical tank suit, but includes an absorbent assembly 54 in the crotch region 32 of the chassis 22, as shown in the partially disassembled, stretched flat view in FIG. 2. The absorbent assembly 54 absorbs liquid insults when the wearer is not immersed in water. Leg elastics 56 can be attached to the chassis 22 about the leg openings 26 for enhanced containment of wastes. Furthermore, containment flaps 58 can also be attached to the chassis 22 about the leg openings 26 for the containment of solid wastes both while the wearer is immersed in water and while the wearer is out of the water.

The one continuous coverstock 50 can be elastic, stretchable or non-stretchable. The one-piece coverstock 50 is suitably stretchable, primarily in a cross-body direction. More suitably the coverstock 50 can have areas of differential stretch to improve fit. For example, desirable areas of greater stretch include the waist region 24 and the buttock region to conform to a wearer's body as the wearer moves about, whereas desirable areas of lesser stretch include areas around the neck opening 48 since typical body movements do not greatly affect the dimensions of a wearer's body around a wearer's neck. Suitable materials for the coverstock 50 of this embodiment include stretchable nonwovens, non-stretchable nonwovens, and nonwoven laminates including spandex and/or stretchable film. Spandex is any of various elastic textile fibers made chiefly of polyurethane. LYCRA® is a brand of spandex commercially available from E.I. du Pont de Nemours and Company, Wilmington, Del., U.S.A. Meltblown laminates are a suitable type of nonwoven laminate.

An embodiment of the swimsuit 20 of the invention having the chassis 22 and the bodice 42 as separate entities is shown in FIG. 3. In this embodiment, the bodice 42 is stretchable and the chassis 22 is non-stretchable. The chassis 22 can either include an absorbent assembly 54 incorporated within the crotch region 32 or simply provide enough room within the chassis 22 to cover a pant-like absorbent article placed on the wearer prior to applying the swimsuit 20 to the wearer.

Figure 4:
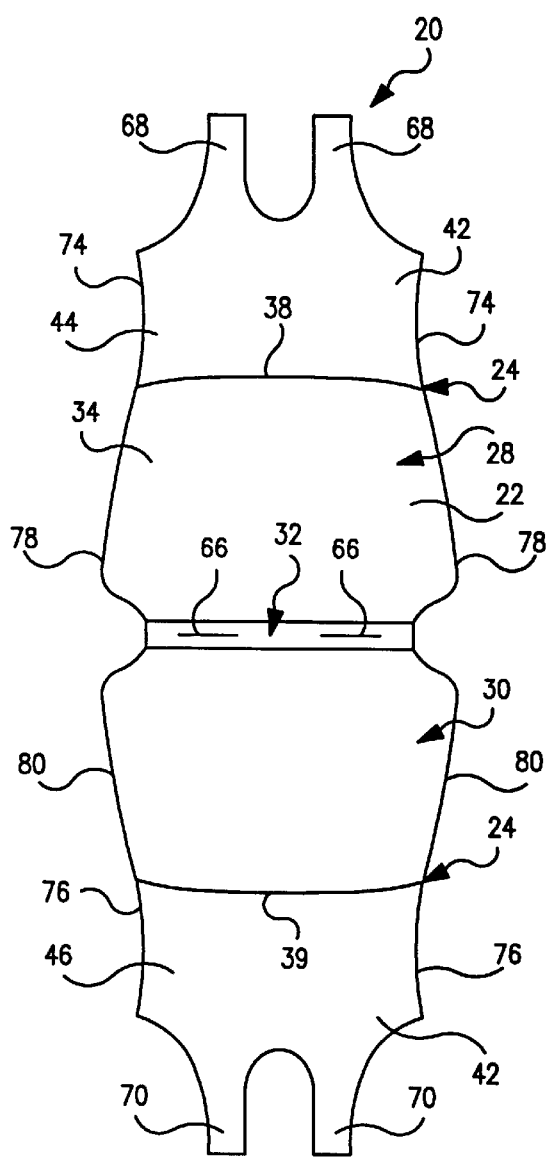
FIG. 4 is a plan view of the one-piece disposable swimsuit in FIG. 3 in a partially disassembled, stretched flat state.
Figure 5:
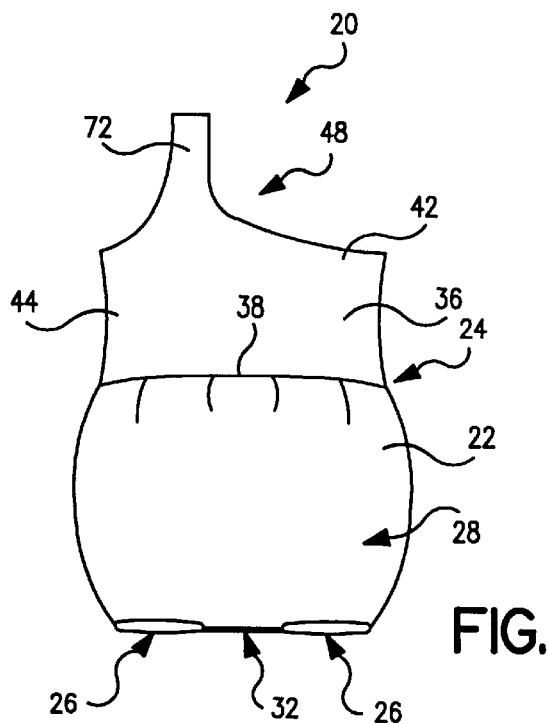
FIG. 5 is a front perspective view of a one-piece disposable swimsuit.

FIG. 4 shows the swimsuit 20 of FIG. 3 in a partially disassembled, stretched flat state. The stretchable material, suitably a stretchable nonwoven, of the bodice 42 is bonded to the non-stretchable material, suitably a non-stretchable nonwoven, of the chassis 22. A narrow band 60 of stretchable material, such as a LYCRA® laminate, is bonded to the chassis 22, suitably from one side of the chassis 22 to an opposite side of the chassis across the crotch region 32. The narrow band 60 of stretchable material can either be bonded to the outer surface 36 or to the inner surface 34. Two slits 66 are cut through the narrow band 60 of stretchable material. These slits 66 define the leg openings 26. The chassis 22, bonded to the bodice 42, is eventually folded in half so that two front strap portions 68 in the front region 44 of the bodice 42 can be bonded to two back strap portions 70 in the back region 46 of the bodice 42, thereby forming two shoulder straps 72. In an alternative embodiment, as shown in FIG. 5, the swimsuit 20 can have a single shoulder strap 72, in which case the one strap can easily be pulled up and over one arm of the wearer, thereby easing the task of donning the swimsuit 20 on the wearer compared to the difficulty that can be encountered with two straps 72. The transverse sides 74 of the front region 44 of the bodice 42 are bonded to the corresponding transverse sides 76 of the back region 46 of the bodice 42, and the transverse sides 78 of the front region 28 of the chassis 22 are bonded to the corresponding transverse sides 80 of the back region 30 of the chassis 22, while the chassis 22 is in the folded state.

The bodice 42 in this embodiment is primarily stretchable in a cross-body direction. As in the previous embodiment, the bodice 42 can have areas of differential stretch to improve fit. The neck opening 48 is suitably large enough for the wearer's torso to fit through it. Suitable materials for the bodice 42 include stretchable nonwovens, and nonwoven laminates including spandex, such as LYCRA® and/or stretchable film. The chassis 22 in this embodiment, although non-stretchable, is suitably roomy, with the leg openings 26 being stretchy to conform to the contour of the wearer's thighs. The roominess of the chassis 22 allows for fitting a wider range of torso lengths, as well as allowing room for a separate pant-like absorbent garment underneath the swimsuit 20. As mentioned, an absorbent assembly 54 can be incorporated within this swimsuit 20 in the crotch region 32, or alternatively, a separate pant-like absorbent garment can be worn beneath the swimsuit 20 such that the pant-like absorbent garment is within the chassis 22.

Another embodiment of the swimsuit 20 of the invention having the chassis 22 and the bodice 42 as separate entities is shown in FIG. 6. In this embodiment, the shoulder strap 72, or straps, includes a fold-over bond. More particularly, as shown in FIG. 7, the straps 72 can be formed from a cross-body cut 82 and folded slightly such that the ends 84 of the front strap portions 68 can be bonded to the ends 86 of the back strap portions 70. Therefore, when using a material for the bodice 42 that has cross-body stretch, the resulting straps 72 will have stretchability perpendicular to the cross-body direction. The stretchability of the straps 72 in this manner allows the straps 72 to conform to a relatively wide range of torso lengths.

Figure 8:
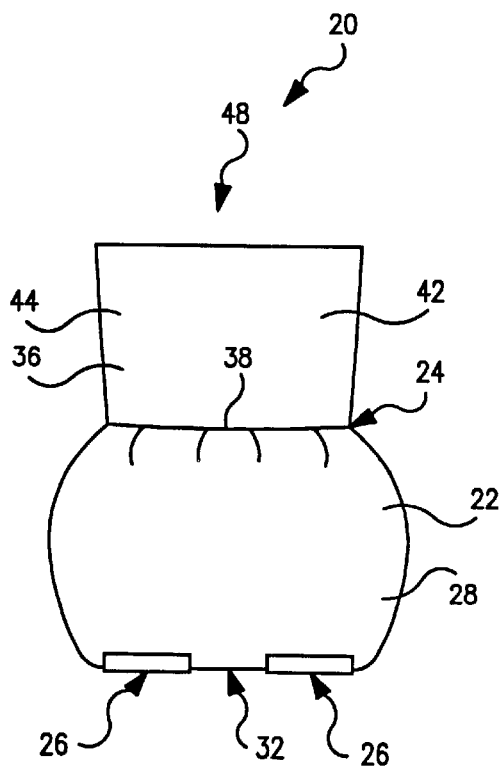
FIG. 8 is a front perspective view of a one-piece disposable swimsuit.
Figure 9:
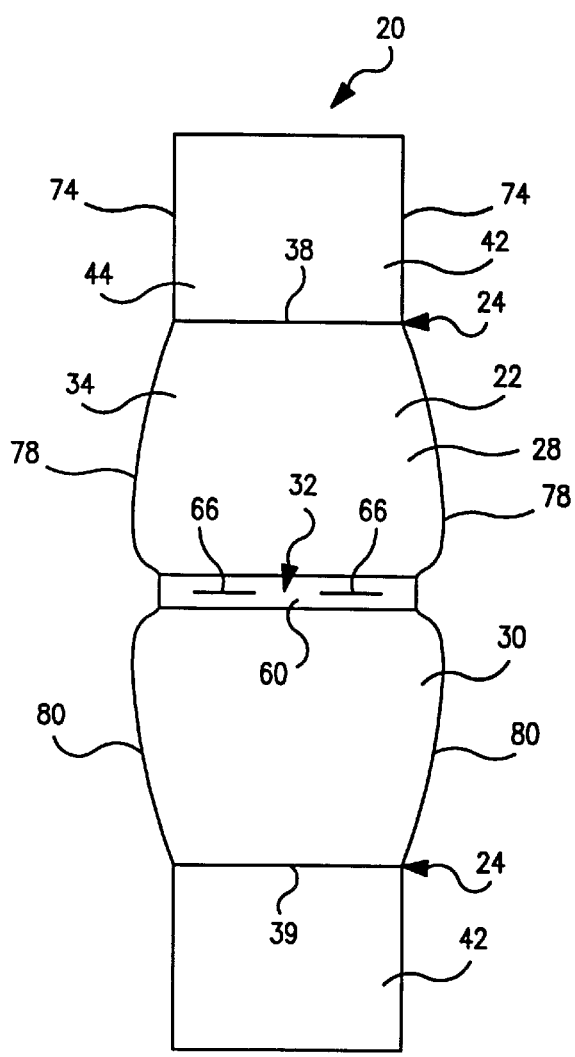
FIG. 9 is a plan view of the one-piece disposable swimsuit in FIG. 8 in a partially disassembled, stretched flat state.

Another embodiment of the swimsuit 20 of the invention is shown in FIG. 8. In this embodiment, the swimsuit 20 does not have any shoulder straps. Instead, the bodice 42 is held in place by the elasticity of the bodice material. In addition, elastic can be added around the top of the bodice for further securing the bodice in place. FIG. 9 shows the swimsuit 20 of FIG. 8 in a partially disassembled, stretched flat state.

Figure 10:
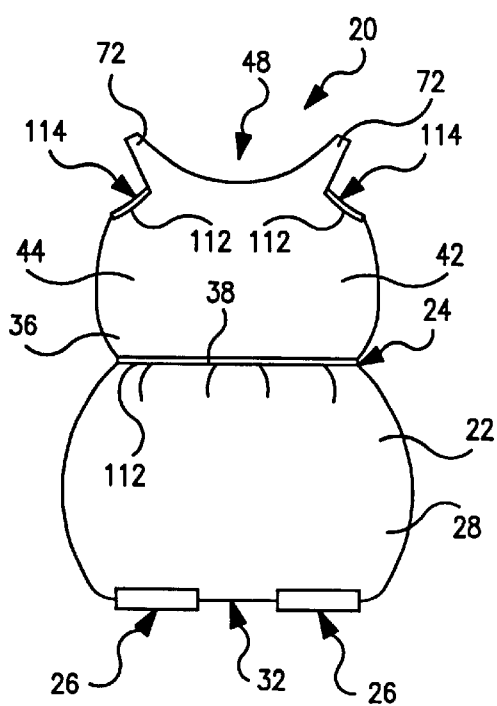
FIG. 10 is a front perspective view of a one-piece disposable swimsuit.
Figure 11:
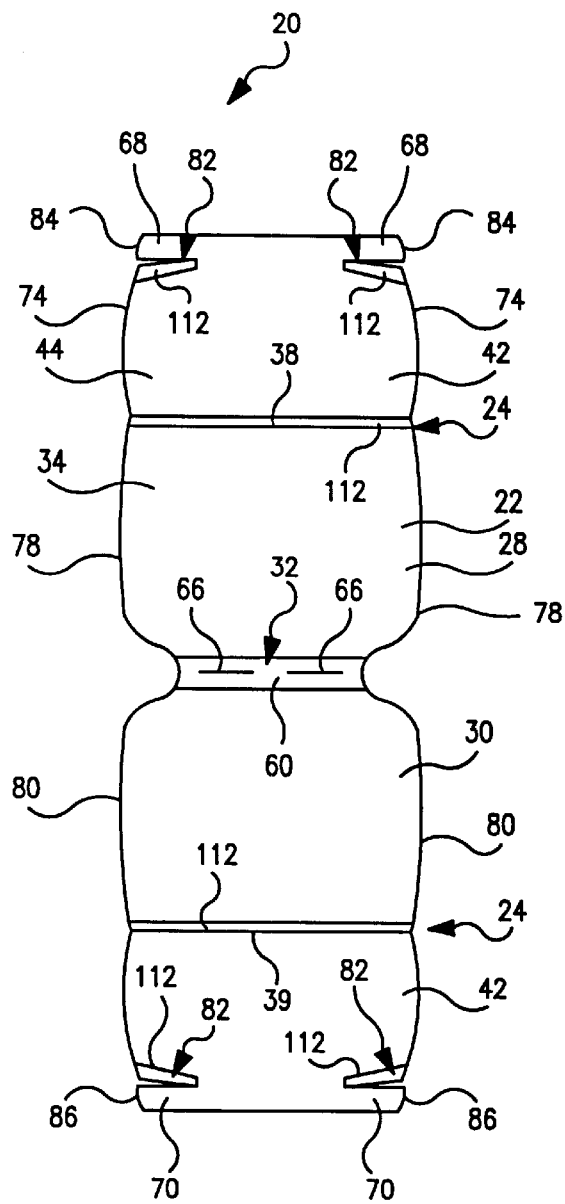
FIG. 11 is a plan view of the one-piece disposable swimsuit in FIG. 10 in a partially disassembled, stretched flat state.

Another embodiment of the swimsuit 20 of the invention is shown in FIG. 10. In this embodiment, the swimsuit 20 has shoulder straps 72 similar to the shoulder straps shown in FIG. 6, but the bodice 42 is inelastic. With both the bodice 42 and the chassis 22 being inelastic, strips of elastic material 112 can be added around the waist region 24 and around the neck opening 48 and/or along underarm edges 114 of the bodice 42 to improve fit without compromising comfort. FIG. 11 shows the swimsuit 20 of FIG. 10 in a partially disassembled, stretched flat state.

Figure 12:
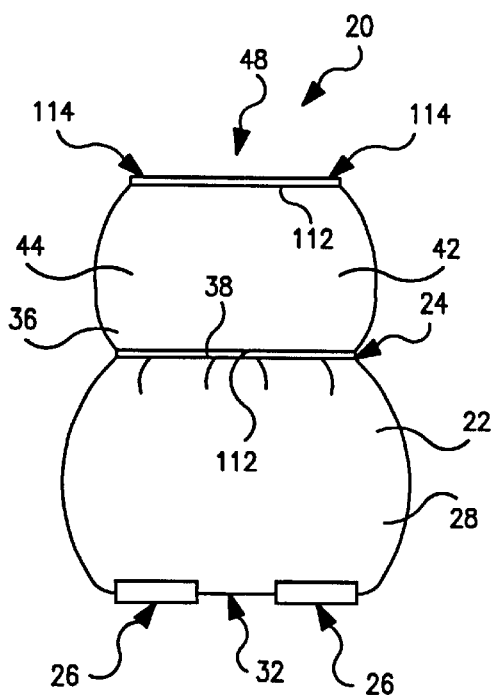
FIG. 12 is a front perspective view of a one-piece disposable swimsuit.
Figure 13:
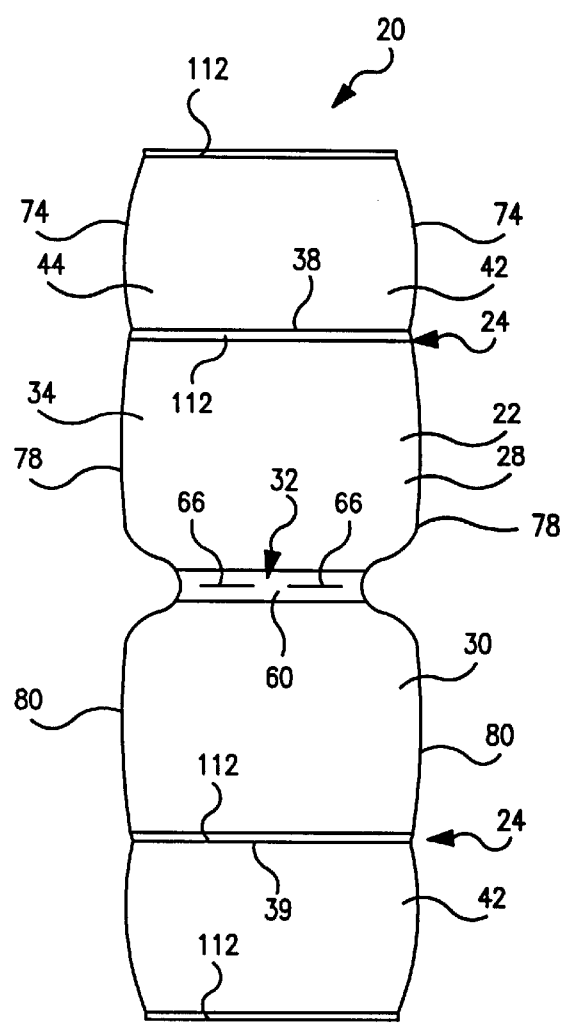
FIG. 13 is a plan view of the one-piece disposable swimsuit in FIG. 12 in a partially disassembled, stretched flat state.

Another embodiment of the swimsuit 20 of the invention is shown in FIG. 12. In this embodiment, the swimsuit 20 has no shoulder straps and has an inelastic bodice 42 and an inelastic chassis 22. With both the bodice 42 and the chassis 22 being inelastic, strips of elastic material 112 can be added around the waist region 24 and across the top of the bodice 42 to improve fit. FIG. 13 shows the swimsuit 20 of FIG. 12 in a partially disassembled, stretched flat state.

Figure 14:
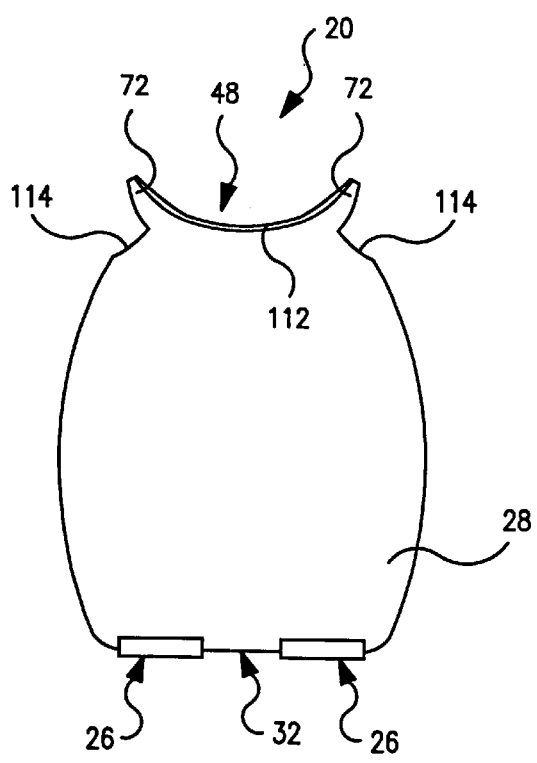
FIG. 14 is a front perspective view of a one-piece disposable swimsuit.

Another embodiment of the swimsuit 20 of the invention is shown in FIG. 14. In this embodiment, the swimsuit 20 has a one-piece, inelastic bodice 42 and chassis 22 with shoulder straps 72. The swimsuit 20 suitably has strips of elastic material 112 along the neck opening 48 and/or along the underarm edges 114 to improve fit.

Figure 15:
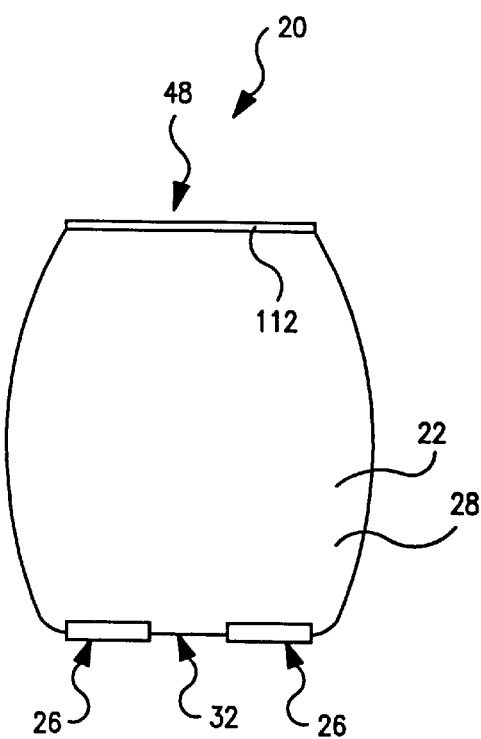
FIG. 15 is a front perspective view of a one-piece disposable swimsuit.

Another embodiment of the swimsuit 20 of the invention is shown in FIG. 15. The swimsuit 20 in this embodiment is similar to the swimsuit 20 shown in FIG. 14, but without the shoulder straps 72. Instead, the swimsuit 20 in this embodiment includes a strip of elastic material 112 across the top of the bodice to improve fit.

Figure 16:
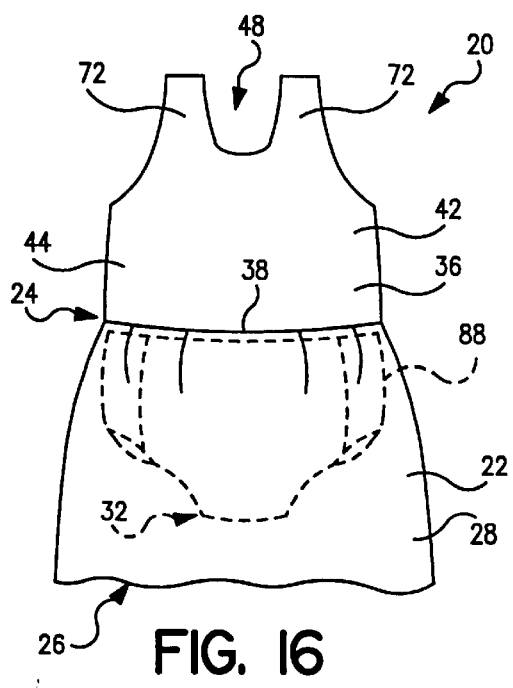
FIG. 16 is a front perspective view of a one-piece disposable swimsuit.

Yet another embodiment of the swimsuit 20 of the invention having the chassis 22 and the bodice 42 as separate entities is shown in FIG. 16. In this embodiment, as in the embodiment shown in FIG. 3, the bodice 42 is stretchable and the chassis 22 is non-stretchable. The chassis 22 in this embodiment is essentially a skirt that provides enough room within the chassis 22 to allow for a separate pant-like absorbent garment 88 underneath, suitably within, the chassis 22.

Figure 17:
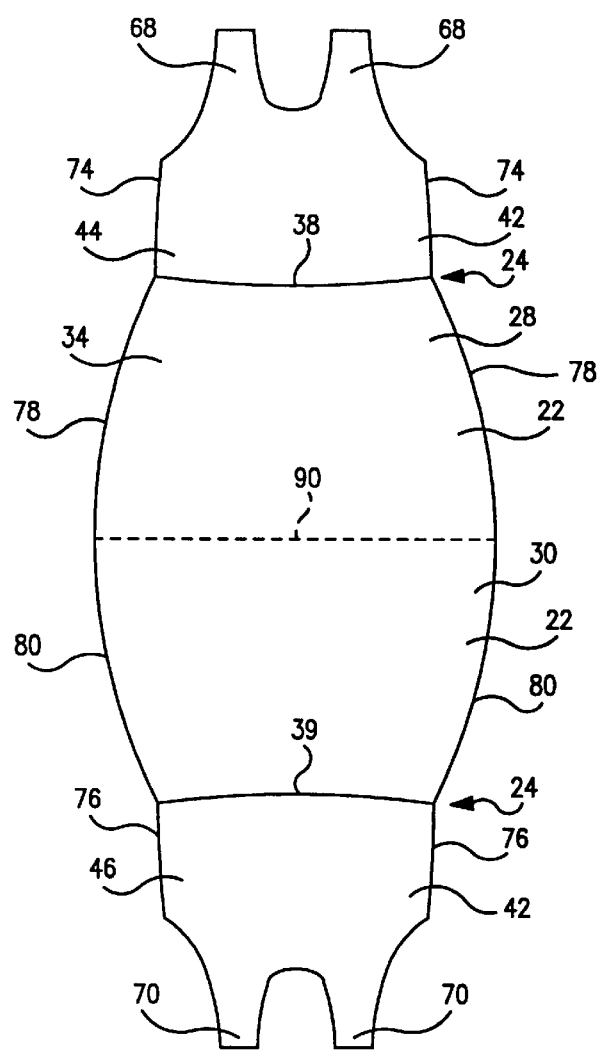
FIG. 17 is a plan view of the one-piece disposable swimsuit in FIG. 16 in a partially disassembled, stretched flat state.

FIG. 17 shows the swimsuit 20 of FIG. 16 in a partially disassembled, stretched flat state. The only difference between the swimsuit 20 shown in FIG. 4 and the swimsuit 20 in FIG. 17 is the narrow band 60 of stretchable material that is present in FIG. 4 and not in FIG. 17. Rather than having a narrow band 60 of stretchable material, the swimsuit 20 in FIG. 17 is instead cut along line 90 where the narrow band 60 would otherwise be attached. Therefore, rather than having two distinct leg openings 26 in the chassis, the chassis 22 essentially has one leg opening 26 large enough to accommodate both of the wearer's legs without restricting leg movement. As in the embodiment shown in FIG. 4, the swimsuit 20 in FIG. 17 is also assembled by aligning the two front strap portions 68 with the two back strap portions 70 and bonding the corresponding strap portions 68, 70 together. Also, the transverse sides 74 of the front region 44 of the bodice 42 are bonded to the corresponding transverse sides 76 of the back region 46 of the bodice 42, and the transverse sides 78 of the front region 28 of the chassis 22 are bonded to the corresponding transverse sides 80 of the back region 30 of the chassis 22.

Figure 18:
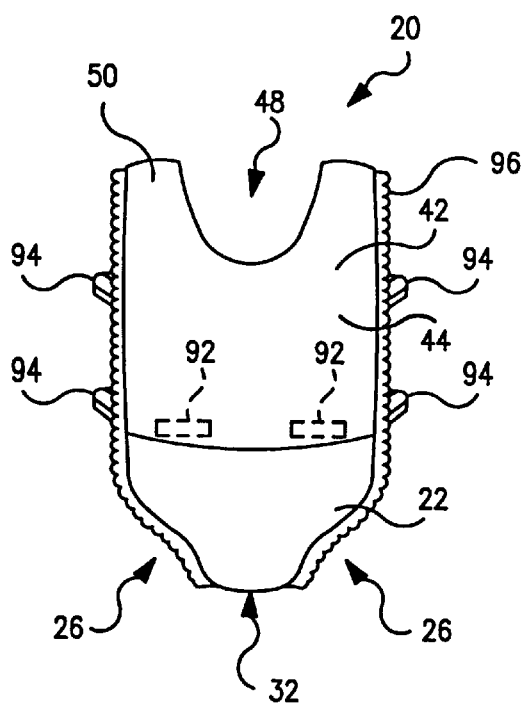
FIG. 18 is a front perspective view of a one-piece disposable swimsuit.
Figure 19:
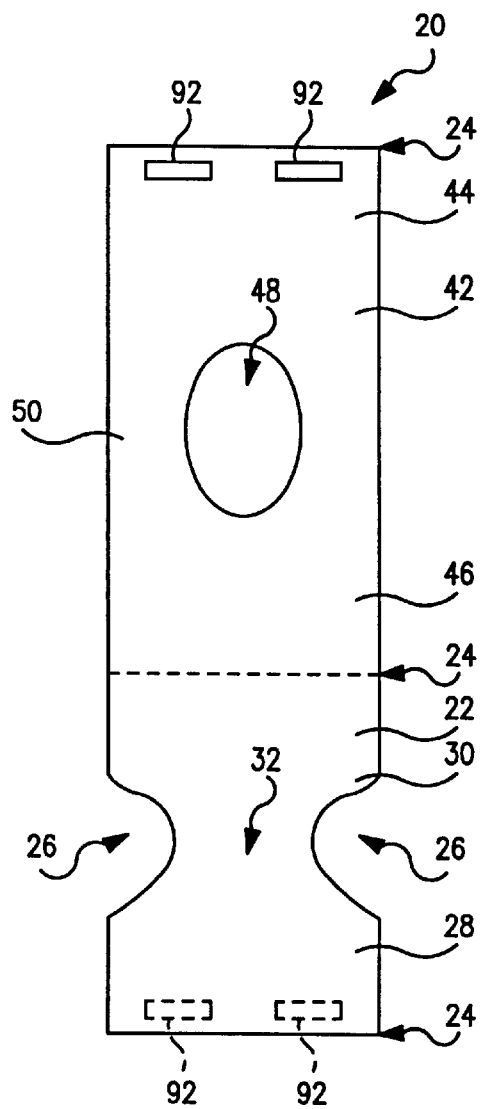
FIG. 19 is a plan view of the one-piece disposable swimsuit in FIG. 18 in a partially disassembled, stretched flat state.

Still another embodiment of the swimsuit 20 of the invention is shown in FIG. 18. In this embodiment, both the bodice 42 and the chassis 22 can be non-stretchable. FIG. 19 shows the swimsuit 20 of FIG. 18 in a partially disassembled, stretched flat state. As shown, the swimsuit 20 can be made of primarily one piece of coverstock 50 with a neck opening 48 and two leg openings 26 cut within the coverstock 50. A refastenable fastening system 92, such as a hook and loop fastener, can be applied to the front region 44 of the bodice 42 along the waist region 24 and to the front region 28 of the chassis 22 along the waist region 24, such that the bodice 42 and the chassis 22 can be releasably engaged to one another. In addition, one or more stretchable bands of material 94 can be attached between the front region 44 of the bodice 42 and the back region 46 of the bodice 42 on either side of the swimsuit 20. Alternatively, or in addition to the stretchable bands of material 94 connecting the front and back regions 44, 46 of the bodice 46, one or more stretchable bands of material 92 can be attached between the front region 28 of the chassis 22 and the back region 30 of the chassis 22 on either side of the swimsuit 20. Optionally, for aesthetic purposes, a gathered portion of non-stretchable material can be attached along the sides of the swimsuit to form a ruffle 96. As in several of the previous embodiments, an absorbent assembly 54 can be incorporated within this swimsuit 20 in the crotch region 32, or alternatively, a separate pant-like absorbent garment can be worn beneath the swimsuit 20 such that the pant-like absorbent garment is within the chassis 22.

Figure 20:
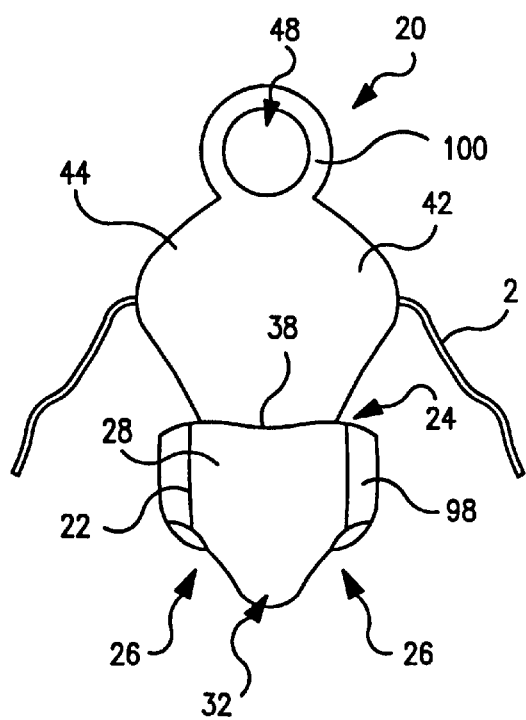
FIG. 20 is a front perspective view of a one-piece disposable swimsuit.
Figure 21:
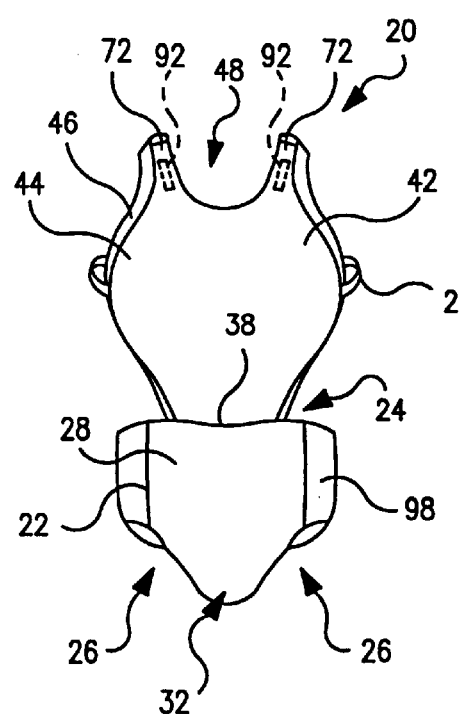
FIG. 21 is a front perspective view of a one-piece disposable swimsuit.

A further embodiment of the swimsuit 20 of the invention is illustrated in FIG. 20. In this embodiment, the chassis 22 is a pant-like absorbent product 98 and is attached to the bodice 42. The pant-like absorbent product 98 can be virtually any type of diaper or training pant, suitably a swimpant such as Little Swimmers® made and sold by Kimberly-Clark Corporation. The bodice 42 can be either a stretchable or a non-stretchable material, suitably a non-woven material of a size sufficient to cover a wearer's upper torso. The bodice 42 can cover the wearer's front upper torso without necessarily covering the wearer's back upper torso, as shown in FIG. 20, but can cover both the front and back upper torso, as shown in FIG. 21, if desired. The bodice includes a neck opening 48, either in the form of a loop 100 that stretches over the wearer's head, as shown in FIG. 20, or defined by one strap 72 or between two straps 72, as shown in FIG. 21. Additionally, either elastic bands or strings or other forms of refastenable fastening systems 92 can be used at the sides of, or around the back of, the wearer's mid-torso region to secure the bodice 42 about the wearer's mid-torso region.

In each of the embodiments of the invention, a refastenable fastening system 92 can be included for greater ease in applying and removing the swimsuit 20. For example, the front strap portion 68 can be releasably attached to the back strap portion 70 using a refastenable fastening system 92, such as a hook and loop fastener, as shown in FIG. 21.

Also in each of the embodiments of the invention, bonding between the bodice 42 and the chassis 22, and/or between front and back regions 44, 46, 28, 30 of the bodice 42 and chassis 22, can be accomplished using attachment means known to those skilled in the art such as adhesive, thermal or ultrasonic bonding.

As mentioned, the swimsuit 20 of the invention can include a pair of elasticized containment flaps 58 (shown in FIG. 2) which are configured to provide a barrier to the transverse flow of body exudates. More particularly, in terms of swimwear, the containment flaps 58 help prevent the escape of bowel movements from the swimsuit 20. Furthermore, the containment flaps 58 provide pre-swim urine leakage protection when the absorbent assembly 54 can no longer acquire the incoming fluid at the rate at which it is being delivered.

The elasticized containment flaps 58 define an unattached edge 106 which assumes an upright, generally perpendicular configuration in at least the crotch region 32 of the swimsuit 20 to form a seal against the wearer's body. Suitable constructions and arrangements for the containment flaps 58 are generally well known to those skilled in the art and are described in U.S. Pat. No. 4,704,116 issued Nov. 3, 1987 to Enloe, which is incorporated herein by reference.

Absorbent swimwear is designed for leakage prevention prior to swimming. Thus, when a wearer wears absorbent swimwear into a pool or lake, the swimwear has a tendency to fill up with water in the crotch region 32. Therefore, the containment flaps 58 of this invention are suitably liquid-permeable to alleviate the build-up of excess swim water within the swimsuit 20 while still retaining any bowel movement or other solid material within the swimsuit.

The absorbent assembly 54 is intended to absorb urine, but does not swell excessively in the presence of swim water, such as pool or lake water. Suitably, the absorbent assembly 54 includes a pulp-based absorbent to prevent excessive swelling when wet. In general, the materials of the absorbent assembly 54 can be configured in various ways to achieve fast intake and to generate void volume in order to prevent excess fluid from reaching the coverstock 50, the containment flaps 58, or any other barrier materials. Furthermore, a dampness-inhibiting spacer layer (not shown) can be located between the absorbent assembly 54 and the coverstock 50. The spacer layer can be made of a hydrophobic foam, for example, to create a three-dimensional structure that maintains an air space within the spacer layer. The air space, partially encapsulated in foam layer interstices, insulates the coverstock 50 from the absorbent assembly 54 and slows heat transfer from a person's fingers to the swimsuit 20, causing the outer surface of the coverstock 50 to feel less clammy and cold. The air space, in combination with the hydrophobic foam dampness-inhibiting material, provides a resilient, soft, springy surface to the fingers, giving an aesthetic improvement over feeling just the wet absorbent assembly 54 beneath the coverstock 50 in the absence of the spacer layer.

The absorbent assembly 54, positioned on the inner surface 34 of the coverstock 50 in the crotch region 32 of the chassis 22, can be any structure which is generally compressible, conformable, non-irritating to the child's skin, and capable of absorbing and retaining liquids and certain body wastes. The absorbent assembly 54 can be manufactured in a wide variety of sizes and shapes, and from a wide variety of liquid absorbent materials commonly used in the art. For example, the absorbent assembly 54 can suitably include a matrix of hydrophilic fibers, such as a web of cellulosic fluff, and the cellulosic fluff may be mixed with particles of a high-absorbency material commonly known as superabsorbent material. In a particular embodiment, the absorbent assembly 54 includes a matrix of cellulosic fluff, such as wood pulp fluff, and synthetic fibers, such as coform or airlaid materials. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 54 to better contain and absorb body exudates. The concentration of the superabsorbent particles can also vary through the thickness of the absorbent assembly 54. Alternatively, the absorbent assembly 54 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 54 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 54 in an amount of from about 0 to about 90 weight percent based on total weight of the absorbent assembly 54. The absorbent assembly 54 suitably has a density within the range of about 0.10 to about 0.35 grams per cubic centimeter. The absorbent assembly 54 may or may not be wrapped or encompassed by a suitable tissue wrap that maintains the integrity and/or shape of the absorbent assembly 54.

The coverstock 50, or outer cover, of both the bodice 42 and the chassis 22 suitably includes a material that is either substantially liquid-permeable or liquid-impermeable, and is desirably at least partially liquid-permeable. More particularly, the material used to make the coverstock 50 can either be liquid-permeable material or can be liquid-impermeable material with holes, pores, or slits added to render the material liquid-permeable over at least part of the surface area. Similarly, the containment flaps 58 are also either liquid-permeable, or liquid-impermeable rendered liquid-permeable through the addition of holes, pores, or slits, for added water drainage capability, or can be liquid-impermeable for greater waste retention prior to swimming.

As mentioned, the coverstock, or outer cover, material 50 can be elastic, stretchable or nonstretchable. For example, the embodiments in FIGS. 1 and 2 have stretchable bodices 42 and chassis 22 of the coverstock 50, while the embodiments in FIGS. 3–7, 16 and 17 have stretchable bodices 42 of the coverstock 50 and non-stretchable chassis 22 of the coverstock 50, and the embodiments in FIGS. 18 and 19 have non-stretchable bodices 42 and chassis 22 of the coverstock 50. The embodiments in FIGS. 8 and 9 have elastic bodices 42 and inelastic chassis 22, such that the bodices 42 are both stretchable and retractable while the chassis 22 may either be stretchable or non-stretchable but in any case cannot retract. Similarly, the embodiments in FIGS. 10–15 have inelastic bodices 42 and inelastic chassis 22, either as separate elements or as one continuous coverstock 50, which can be either stretchable or non-stretchable but cannot retract.

The stretchable material can be a nonwoven laminate including a stretchable film. Suitable stretchable polymers for making the film include stretchable olefin polymers, such as an olefinic copolymer of polyethylene. More specifically, other stretchable polymers include diblock, triblock, tetrablock or other multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from the Shell Chemical Company, under the trade designation KRATON® elastomeric resin; polyurethanes, including those available from E.I. Du Pont de Nemours Co., under the trade name LYCRA® polyurethane; polyamides, including polyether block amides available from Ato Chemical Company, under the trade name PEBAX® polyether block amide; polyesters, such as those available from E.I. Du Pont de Nemours Co., under the trade name HYTREL® polyester; and single-site or metallocene-catalyzed polyolefins having density less than about 0.89 grams/cc, available from Dow Chemical Co. under the trade name AFFINITY®.

Examples of suitable types of laminates include a meltblown laminate, a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the stretchable material may include other woven or nonwoven materials. The non-stretchable materials for this invention are suitably nonwoven.

The coverstock 50 can be a single layer of material or a multi-layered laminate structure. For instance, the coverstock 50 can include a liquid permeable outer layer and a liquid permeable inner layer that are suitably joined together by a laminate adhesive (not shown) or by thermal bonding or any other suitable attachment means. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. If the outer layer and the inner layer include holes or other types of incisions to provide the permeability, the holes of the layers as assembled are desirably offset from one another to hinder the permeability of fluids under low hydrostatic pressure.

The liquid permeable outer layer can be any suitable material and desirably one that provides a generally cloth-like texture. One example of such a material is a spunbond polypropylene nonwoven web having a basis weight of about 1–100 gsm (grams per square meter), suitably 10–50 gsm, desirably 15–25 gsm. While it is not a necessity for the outer layer to be substantially liquid permeable, it is desired that it provides a relatively cloth-like texture to the wearer. Other examples include polyolefin or other thermoplastic nonwoven webs having basis weights in the same ranges, including spunbond webs, meltblown webs, bonded carded webs, airlaid webs, and combinations of the foregoing, such as spunbond/meltblown webs and spunbond/meltblown/spunbond webs. Another material feature that may be desirable in the outer layer is the inclusion of sun protection factor (SPF) in the fabric, thus providing protection from sunburn under the garment.

The inner layer of the coverstock 50 is desirably manufactured from a thin plastic film, although other flexible materials may also be used. The inner layer can line the entire area of the outer layer of the coverstock 50 or can cover just a portion of the outer layer of the coverstock 50. As with the coverstock 50 as a whole, holes or other incisions can be made in the inner layer to render the inner layer liquid-permeable, Breathability is another material feature that may be desirable in the coverstock 50. An example of a suitable liquid impermeable film for use as a liquid impermeable inner layer, or a single layer liquid impermeable coverstock 50, is a 0.02 millimeter polyethylene film commercially available from Huntsman Packaging of Newport News, Va., U.S.A. If the coverstock 50 is a single layer of material, it can be embossed and/or matte finished to provide a more cloth-like appearance.

When an absorbent assembly 54 is incorporated within the swimsuit 20, a body side liner 108 can also be incorporated in the swimsuit 20, such that the absorbent assembly 54 is located between the coverstock 50 and the body side liner 108 in the crotch region 32 of the swimsuit 20. The body side liner 108 can partially or entirely line the swimsuit 20, but should cover at least the entirety of the absorbent assembly 54. FIG. 2 shows the body side liner 108 lining the chassis 22 and not the bodice 42. The body side liner 108 is desirably compliant, soft feeling, and non-irritating to the wearer's skin. Further, the body side liner 108 can be less hydrophilic than the absorbent assembly 54, to present a relatively dry surface to the wearer and permit liquid to readily penetrate through its thickness.

The body side liner 108 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 108. For example, the body side liner 108 can be composed of a meltblown or spunbonded web of polyolefin fibers. The body side liner 108 can also be a bonded-carded web composed of natural and/or synthetic fibers. The body side liner 108 can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire body side liner 108 or can be selectively applied to particular sections of the body side liner 108, such as the medial section along the longitudinal centerline.

A suitable liquid permeable body side liner 108 is a nonwoven bicomponent web having a basis weight of about 27 gsm. The nonwoven bicomponent can be a spunbond bicomponent web, or a bonded carded bicomponent web. Alternatively, the body side liner 108 can be a 15–30 gsm homofilament polypropylene spunbond or bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the coverstock 50 and body side liner 108 can include elastomeric materials, it can be desirable in some embodiments, such as those shown in FIGS. 18 and 19, for the composite structure to be generally inelastic, where the coverstock 50, the body side liner 108 and the absorbent assembly 54 include materials that are generally not elastomeric.

The containment flaps 58 may be made of those materials of which the coverstock 50 and/or the body side liner 108 is made, or other suitable materials.

The swimsuit 20 is suitably made of relatively inexpensive materials, such as spunbonded nonwovens, stable fiber nonwovens, or hydroentangled nonwovens. However, these materials are typically destroyed after their intended use, thereby rendering the swimsuit 20 disposable.

To further enhance containment and/or absorption of body exudates, the swimsuit 20, in any of its embodiments, can include leg elastics 56, as are known to those skilled in the art (FIG. 2). The leg elastics 56 are desirably operatively joined to the coverstock 50 and/or to the body side liner 108 longitudinally adjacent the leg openings 26 in the crotch region 32 of the swimsuit 20.

The leg elastics 56 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastics 56 include a plurality of dry-spun coalesced multifilament spandex elastomeric threads sold under the trade name LYCRA® and available from E.I. du Pont de Nemours and Company, Wilmington, Del., U.S.A. In another particular embodiment, for example, the leg elastics 56 include Findley HX 2695-01 adhesive laminated to two facings of 0.4 osy polypropylene spunbond. Alternatively, strands of 310 decitex LYCRA® may be also laminated at about 50% to 300% elongation between the spunbond facings in addition to the Findley adhesive.

As described herein, the various components of the swimsuit 20 can be integrally assembled together employing various types of suitable attachment means, such as adhesive, sonic and thermal bonds or combinations thereof. The resulting product is a disposable swimwear garment 20 that provides upper torso coverage, along with absorbent and containment features.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A disposable swimwear garment comprising:
   a chassis defining a waist region and first and second leg openings, the chassis including a front waist edge bonded to a back waist edge such that the waist opening encircles a wearer's waist, and an absorbent assembly between the first and second leg opening wherein the absorbent asembly is selected from a web comprising cellulosic fluff and a web comprising superabsorbent material; and
   a bodice defining a neck opening, the bodice attached to the chassis at the waist region.

2. The swimwear garment of claim 1, further comprising a one-piece coverstock defining the chassis and the bodice.

3. The swimwear garment of claim 2, wherein the coverstock comprises a stretchable nonwoven web.

4. The swimwear garment of claim 2, wherein the coverstock comprises areas of differential stretch.

5. The swimwear garment of claim 2, wherein the coverstock comprises spandex.

6. The swimwear garment of claim 2, wherein the coverstock comprises a stretchable film.

7. The swimwear garment of claim 2, wherein the coverstock comprises a meltblown laminate.

8. The swimwear garment of claim 1, wherein the absorbent assembly comprises a pulp-based absorbent.

9. The swimwear garment of claim 1, further comprising a pair of containment flaps attached to the chassis about the first and second leg openings.

10. The swimwear garment of claim 9, wherein the containment flaps are liquid-permeable.

11. A disposable swimwear garment comprising:
    a non-stretchable chassis defining a waist region and at least one leg opening, the chassis including a front waist edge bonded to a back waist edge such that the waist region encircles a wearer's waist;
    an absorbent assembly within the chassis wherein the absorbent assembly is selected from a web comprising cellulosic fluff and a web comprising superabsorbent material; and
    a bodice defining a neck opening, the bodice attached to the chassis at the waist region.

12. The swimwear garment of claim 11, further comprising first and second leg openings.

13. The swimwear garment of claim 12, wherein the chassis further comprises a band of stretchable material having at least two slits within the band of stretchable material, the slits defining the first and second leg openings.

14. The swimwear garment of claim 11, wherein the at least one leg opening is large enough to fit around two legs.

15. The swimwear garment of claim 11, wherein the bodice comprises a spunbonded nonwoven.

16. The swimwear garment of claim 11, wherein the bodice comprises a stable fiber nonwoven.

17. The swimwear garment of claim 11, wherein the bodice comprises a hydroentangled nonwoven.

18. The swimwear garment of claim 11, wherein the chassis comprises a spunbonded nonwoven.

19. The swimwear garment of claim 11, wherein the chassis comprises a stable fiber nonwoven.

20. The swimwear garment of claim 11, wherein the chassis comprises a hydroentangled nonwoven.

21. The swimwear garment of claim 11, comprising at least one shoulder strap.

22. The swimwear garment of claim 21, wherein the at least one shoulder strap comprises a fold-over bond.

23. The swimwear garment of claim 21, further comprising a refastenable fastening system between a front portion of the at least one shoulder strap and a back portion of the at least one shoulder strap.

24. The swimwear garment of claim 11, comprising at least two shoulder straps.

25. The swimwear garment of claim 11, further comprising at least two stretchable bands between a front region of the bodice and a back region of the bodice.

26. The swimwear garment of claim 25, further comprising a refastenable fastening system between the bodice and the chassis.

27. The swimwear garment of claim 11, wherein the absorbent assembly comprises a pulp-based absorbent.

28. The swimwear garment of claim 11, wherein the absorbent assembly comprises a pant-like absorbent product.

29. The swimwear garment of claim 28, wherein the pant-like absorbent product is unattached to the swimwear garment and the chassis is configured to fit over the pant-like absorbent product.

30. A disposable swimwear garment comprising:

a pant-like absorbent product defining a waist region and first and second leg openings an absorbent assembly within the pant-like absorbent product, wherein the absorbent assembly is selected from a web comprising cellulosic fluff and a web comprising superabsorbent material; and a bodice defining a neck opening, the bodice attached to the chassis at the waist region.

31. The swimwear garment of claim 30, wherein the bodice comprises a non-stretchable nonwoven web.

32. The swimwear garment of claim 30, wherein the bodice comprises a stretchable nonwoven web.

33. The swimwear garment of claim 30, wherein the bodice includes a front portion.

34. The swimwear garment of claim 33, further comprising at least one fastening device attached to the bodice for fastening behind a wearer's back.

35. The swimwear garment of claim 30, wherein the bodice includes a front portion and a back portion.

* * * * *

UNITED STATES PATENT AND TRADEMARK OFFICE
CERTIFICATE OF CORRECTION

PATENT NO.    : 6,582,412 B2                                                          Page 1 of 1
DATED         : June 24, 2003
INVENTOR(S)   : Sarah L. Christoffel et al.

It is certified that error appears in the above-identified patent and that said Letters Patent is hereby corrected as shown below:

Column 14,
Line 2, should read -- bodice comprises a staple fiber nonwoven. --
Line 6, should read -- between the first and second leg openings wherein the --

Column 15,
Line 2, should read -- chassis comprises a staple fiber nonwoven. --

Column 16,
Line 3, should read -- first and second leg openings; an absorbent assembly --

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,582,412 B2
DATED : June 24, 2003
INVENTOR(S) : Sarah L. Christoffel et al.

It is certified that error appears in the above-identified patent and that said Letters Patent is hereby corrected as shown below:

Column 14,
Line 20, should read -- bodice comprises a staple fiber nonwoven. --
Line 67, should read -- between the first and second leg openings wherein the --

Column 15,
Line 6, should read -- chassis comprises a staple fiber nonwoven. --

Column 16,
Line 7, should read -- first and second leg openings; an absorbent assembly --

This certificate supersedes Certificate of Correction issued September 16, 2003

Signed and Sealed this

Thirtieth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,582,412 B2  
DATED : June 24, 2003  
INVENTOR(S) : Sarah L. Christoffel et al.

Page 1 of 1

It is certified that error appears in the above-identified patent and that said Letters Patent is hereby corrected as shown below:

<u>Column 14,</u>  
Line 20, should read -- between the first and second leg openings wherein the --  
Line 67, should read -- bodice comprises a staple fiber nonwoven. --

<u>Column 15,</u>  
Line 6, should read -- chassis comprises a staple fiber nonwoven. --

<u>Column 16,</u>  
Line 7, should read -- first and second leg openings; an absorbent assembly --

This certificate supersedes Certificate of Correction issued December 30, 2003

Signed and Sealed this

Thirtieth Day of March, 2004

JON W. DUDAS  
*Acting Director of the United States Patent and Trademark Office*